(12) United States Patent
Tanaka

(10) Patent No.: US 11,705,646 B2
(45) Date of Patent: Jul. 18, 2023

(54) CONNECTION STRUCTURE BETWEEN SENSOR AND CABLE, AND CONNECTION CABLE

(71) Applicant: HIRAKAWA HEWTECH CORPORATION, Tokyo (JP)

(72) Inventor: Hiroyuki Tanaka, Koga (JP)

(73) Assignee: HIRAKAWA HEWTECH CORPORATION, Tokyo (JP)

( * ) Notice: Subject to any disclaimer, the term of this patent is extended or adjusted under 35 U.S.C. 154(b) by 121 days.

(21) Appl. No.: 17/000,775

(22) Filed: Aug. 24, 2020

(65) Prior Publication Data

US 2021/0066820 A1 Mar. 4, 2021

(30) Foreign Application Priority Data

Aug. 28, 2019 (JP) .................. 2019-155771

(51) Int. Cl.
*G01J 1/44* (2006.01)
*H01R 4/02* (2006.01)
*H01R 4/04* (2006.01)

(52) U.S. Cl.
CPC ............ *H01R 4/023* (2013.01); *G01J 1/44* (2013.01); *H01R 4/029* (2013.01); *H01R 4/04* (2013.01); *G01J 2001/448* (2013.01)

(58) Field of Classification Search
CPC .......... H01R 4/023; H01R 4/029; H01R 4/04; H01R 12/53; H01R 4/027; G01J 1/44; G01J 2001/448; A61B 1/00114
See application file for complete search history.

(56) References Cited

U.S. PATENT DOCUMENTS

| 4,677,471 | A | 3/1987 | Takamura et al. |
| 8,072,537 | B2 | 12/2011 | Schwarz et al. |
| 2003/0220574 | A1 | 11/2003 | Markus et al. |
| 2009/0021618 | A1 | 1/2009 | Schwarz et al. |

(Continued)

FOREIGN PATENT DOCUMENTS

| EP | 2 018 043 A1 | 1/2009 |
| JP | S62-40414 A | 2/1987 |

(Continued)

OTHER PUBLICATIONS

Extended European Search Report dated Dec. 18, 2020 for European Patent Application No. 20191668.1-1122.

(Continued)

*Primary Examiner* — Kevin K Pyo
(74) *Attorney, Agent, or Firm* — McGinn I.P. Law Group, PLLC

(57) ABSTRACT

A connection structure between sensor and cable includes a cable formed by assembling a plurality of electric wires each including a covering portion covering a core and a core-exposing portion exposing the core at an end of the covering portion, a spacer that is interposed in a space surrounded by the covering portions of the electric wires and holds end portions of the covering portions in the state that the end portions are spaced from each other, and a sensor that detects a physical quantity, and the core-exposing portion of each of the electric wires of the cable is electrically connected to the sensor via a fixing member in the state that each of the electric wires is held by the spacer.

23 Claims, 11 Drawing Sheets

(56) References Cited

U.S. PATENT DOCUMENTS

| | | | | |
|---|---|---|---|---|
| 2009/0223041 | A1* | 9/2009 | Garrison | H01R 12/63 29/755 |
| 2013/0233616 | A1* | 9/2013 | Okuyama | H02G 15/007 174/652 |
| 2016/0365166 | A1* | 12/2016 | Oh | H01B 7/17 |
| 2017/0155860 | A1* | 6/2017 | Ishizuka | H01R 13/22 |
| 2019/0348770 | A1* | 11/2019 | Sato | G02B 23/2484 |
| 2020/0000328 | A1 | 1/2020 | Sakai et al. | |
| 2020/0084343 | A1 | 3/2020 | Sekido | |
| 2020/0203854 | A1* | 6/2020 | Tamura | A61B 1/0011 |

FOREIGN PATENT DOCUMENTS

| | | |
|---|---|---|
| JP | S62-98318 A | 5/1987 |
| JP | H05-154099 A | 6/1993 |
| JP | H10-172628 A | 6/1998 |
| JP | 2009-027709 A | 2/2009 |
| JP | 2014-158563 A | 9/2014 |
| JP | 2017-047169 A | 3/2017 |
| JP | 2017-195965 A | 11/2017 |
| JP | 2019-195451 A | 11/2019 |
| KR | 10-1972864 B1 | 4/2019 |
| WO | WO 2018/158897 A1 | 9/2018 |
| WO | WO 2018/173261 A1 | 9/2018 |
| WO | WO 2018/173323 A1 | 9/2018 |

OTHER PUBLICATIONS

Japanese Office Action dated Nov. 26, 2019 for Japanese Patent Application No. 2019-155771, and English Translation thereof.

* cited by examiner

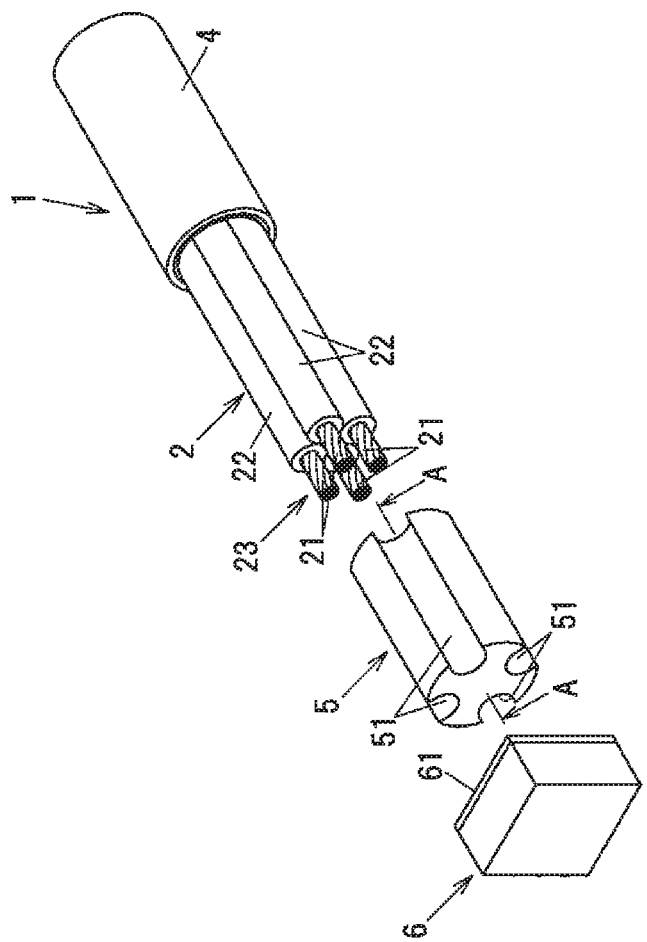
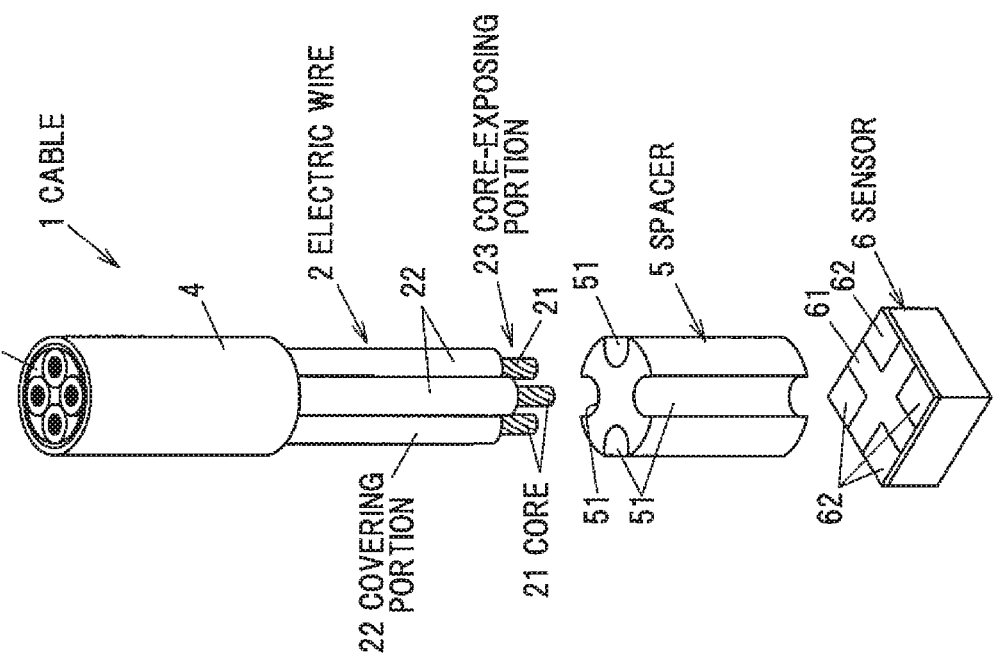

FIG. 3A
FIG. 3B
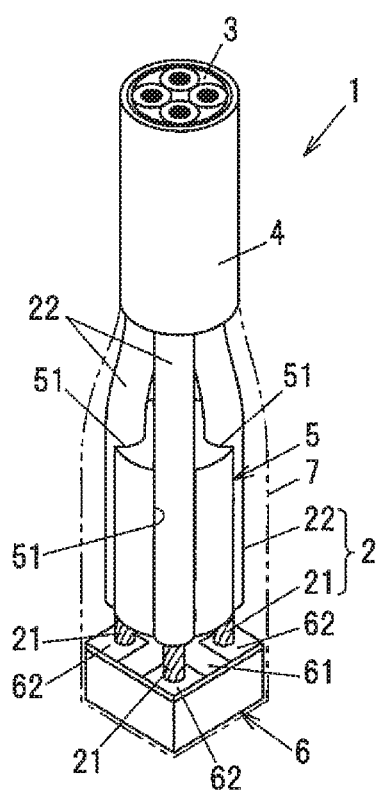
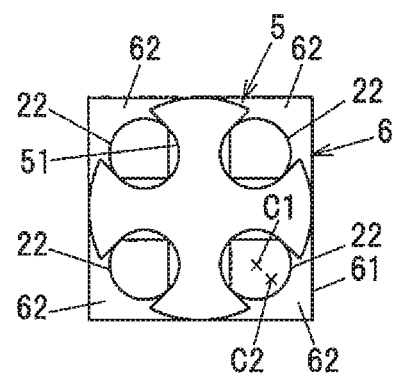

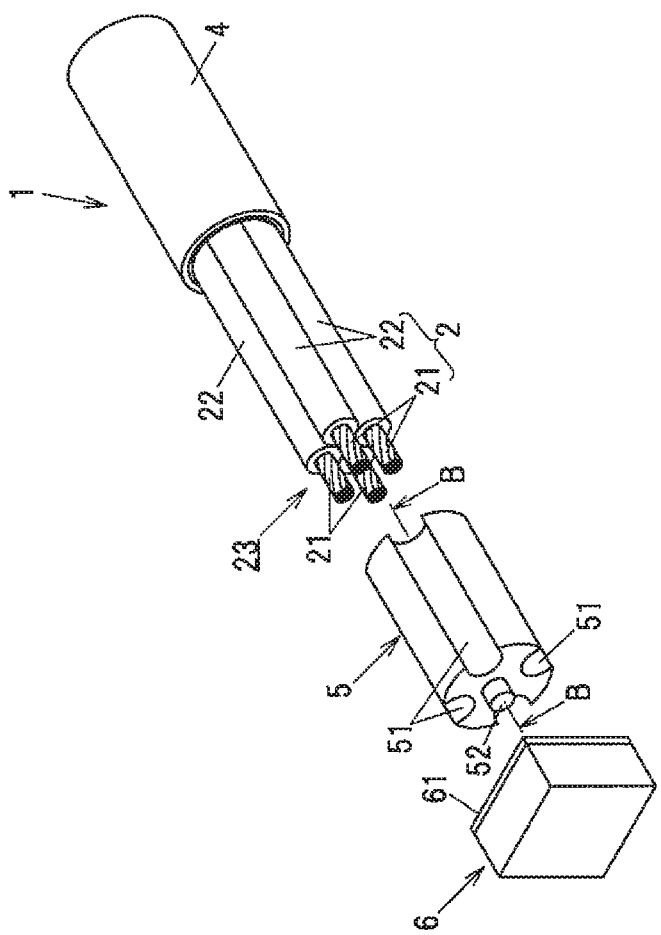
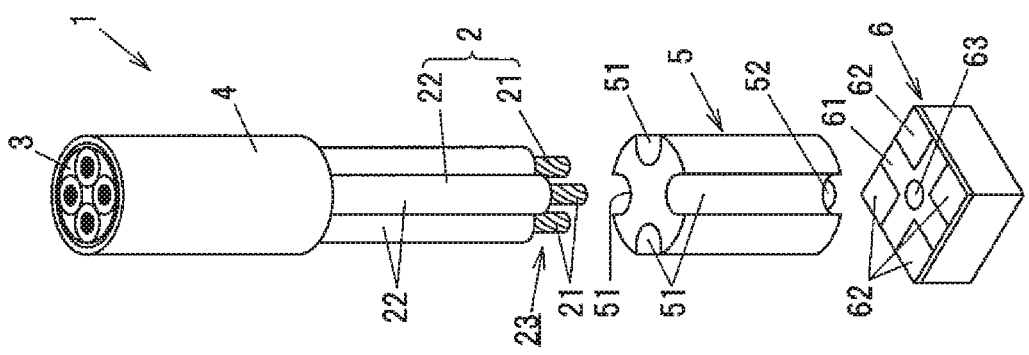

FIG. 6A
FIG. 6B
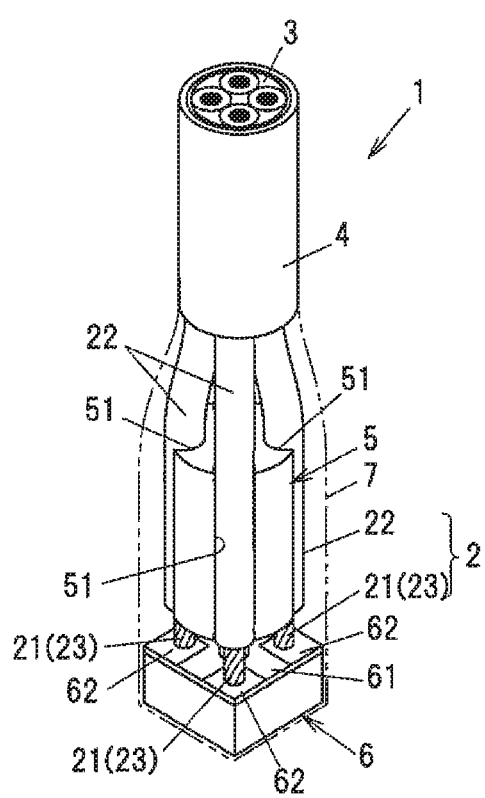
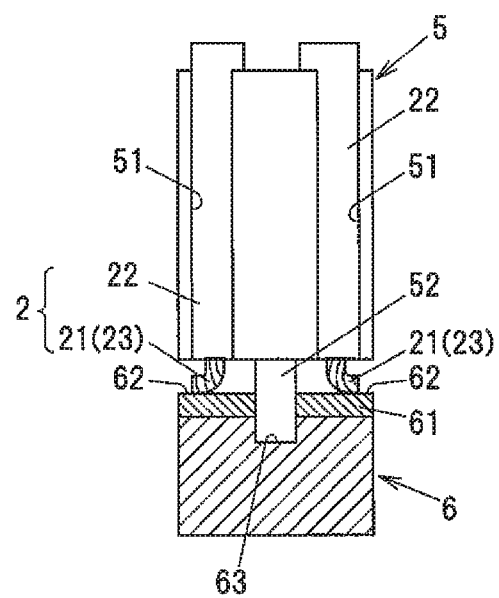

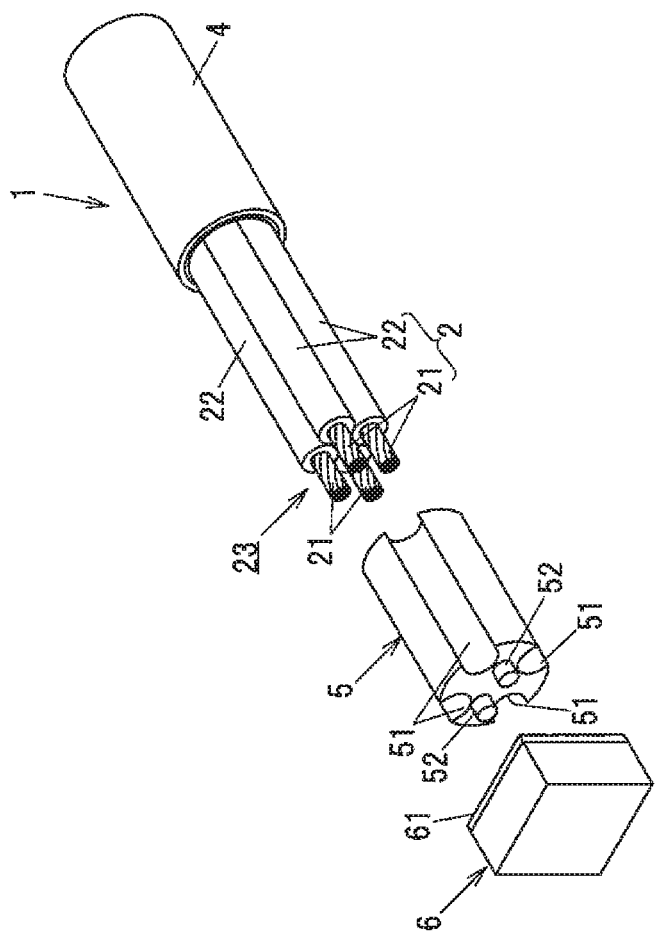
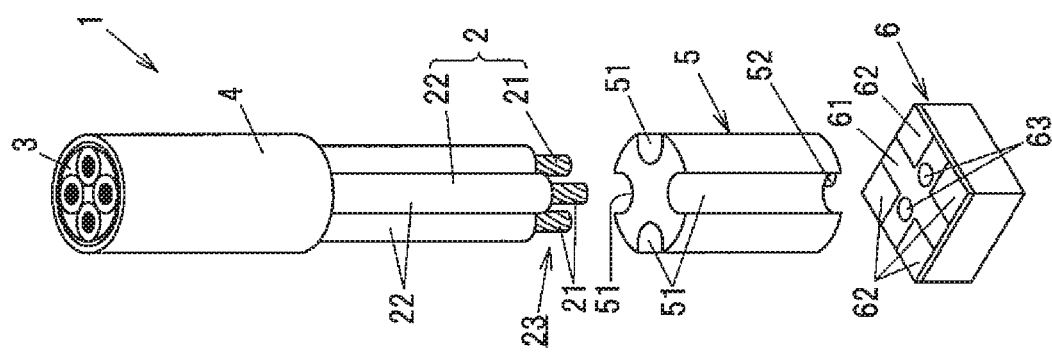
FIG. 7B
FIG. 7A

FIG. 9A
FIG. 9B
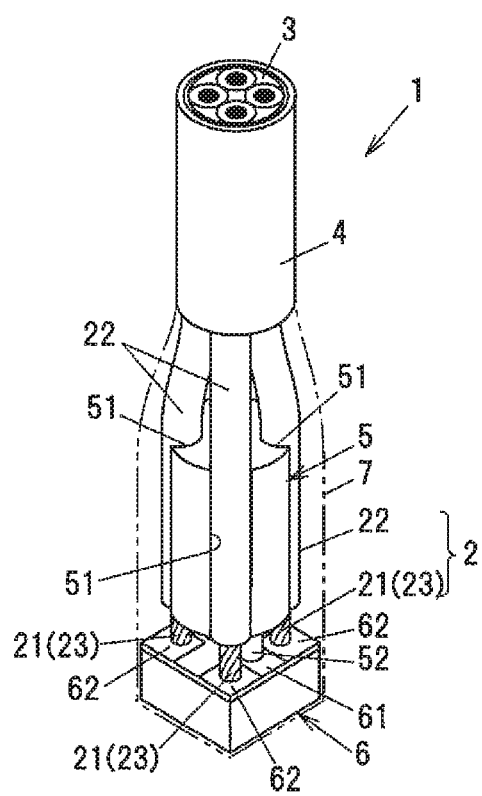
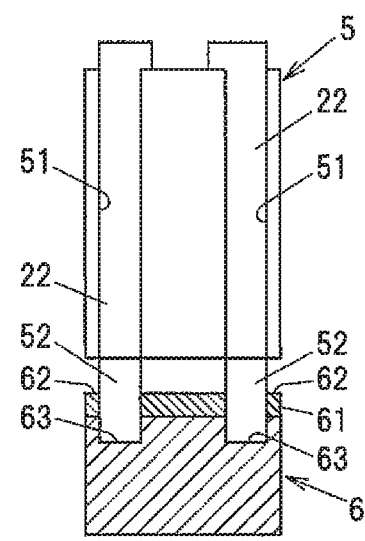
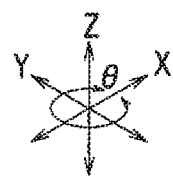

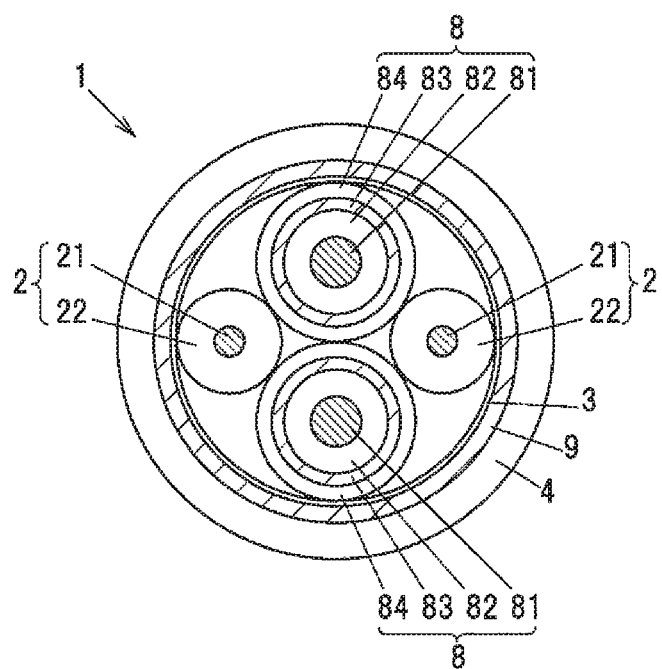
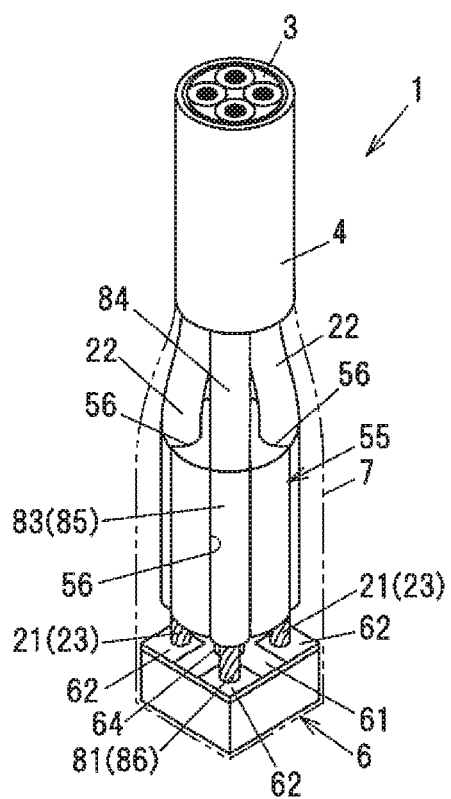
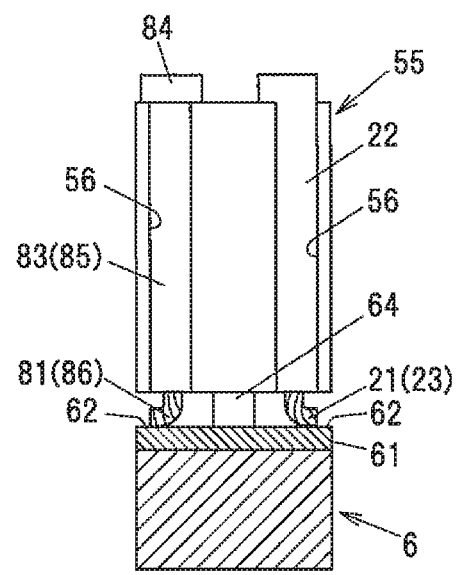
FIG. 10A
FIG. 10B
FIG. 10C

CONNECTION STRUCTURE BETWEEN SENSOR AND CABLE, AND CONNECTION CABLE

CROSS-REFERENCE TO RELATED APPLICATION

The present application is based on Japanese Patent Application No.2019-155771 filed on Aug. 28, 2019, the entire contents of which are incorporated herein by reference.

BACKGROUND OF THE INVENTION

1. Field of the Invention

The invention relates to a connection structure between sensor and cable, and a connection cable, in particular, to a connection structure between a physical quantity detection sensor and a cable having plural cores (core wires), and a connection cable applicable to the connection structure. In more detail, the invention relates to a connection structure between a medical microsensor and a super fine cable, and the super fine cable to be connected to the medical microsensor.

2. Description of the Related Art

In recent years, medical microsensors provided with CCD (Charge-Coupled Device) or CMOS (Complementary MOS) as an image sensor element, such as CCD sensors or CMOS sensors, are often used for medical devices which are inserted into the body and typified by medical endoscopes or sensor-equipped catheters. An example of a connection structure in which a transmission cable having plural cores is electrically connected to such a sensor is disclosed (see, e.g., JP2017-47169A).

The connection structure between the image sensor element and the transmission cable described in JP 2017-47169A is configured that four cores of the transmission cable are soldered and electrically connected, one by one, to four conductor connecting portions provided on a surface of the image sensor element on the opposite side to an imaging surface.

For connecting plural cores of a cable to a microsensor which is used mainly for a medical endoscope or a sensor-equipped catheter and is inserted into the body, a peripheral space for connecting the plural cores is limited and connection work is difficult. For this reason, well-trained workers with very high skills generally manually carry out such work.

However, it is necessary to spend a long time not only for this connection work but also for developing highly-skilled workers. Thus, mass production is difficult and it is difficult to meet a sudden increase in production. Furthermore, since it is manual work, the manufacturing cost is high and variations in connection accuracy or connection strength may occur.

In addition, during the conventional work of connecting the plural cores of the cable one by one to the microsensor, wire breakage, etc., often occurs since, e.g., stress (load) is applied to the first core when the second core is connected after connecting the first core. As one of the causes, it is considered that particularly the cable to be connected to the sensor is super fine.

SUMMARY OF THE INVENTION

Therefore, it is an object of the invention to provide a connection structure between sensor and cable which can reduce the manufacturing cost by facilitating work of connecting a cable to a sensor and can provide improved connection accuracy and connection strength, and a connection cable applicable to the connection structure.

To achieve the above-mentioned object, a connection structure between sensor and cable according to the invention comprises a cable comprising a plurality of electric wires each comprising a covering portion covering a core and a core-exposing portion exposing the core at an end of the covering portion; a spacer that is interposed in a space surrounded by the covering portions of the electric wires and holds end portions of the covering portions in the state that the end portions are spaced from each other; and a sensor that detects a physical quantity, wherein the core-exposing portion of each of the electric wires of the cable is electrically connected to the sensor via a fixing member in the state that each of the electric wires is held by the spacer.

In the connection structure between sensor and cable according to the invention, the spacer may have an outer circumferential surface on which a plurality of holding recesses are spaced from each other in a circumferential direction.

In the connection structure between sensor and cable according to the invention, the spacer may have an end face on which a contact portion configured to be in contact with the sensor is provided.

In the connection structure between sensor and cable according to the invention, the sensor may have a positioning portion for positioning with respect to the contact portion.

In the connection structure between sensor and cable according to the invention, a surface of the spacer may be electrically conductive.

In the connection structure between sensor and cable according to the invention, the fixing member may be solder or conductive adhesive.

In the connection structure between sensor and cable according to the invention, the sensor may be a CCD sensor or a CMOS sensor. In the connection structure between sensor and cable according to the invention, the sensor may be an infrared sensor or an ultrasonic transducer or a fluorescence sensor. In the connection structure between sensor and cable according to the invention, the sensor may be a semiconductor sensor. In the connection structure between sensor and cable according to the invention, the sensor may be provided with an image sensor element.

In the connection structure between sensor and cable according to the invention, when the electric wire is a shield wire provided with a shield layer, the shield layer may be electrically connected to the conductive surface of the spacer.

In the connection structure between sensor and cable according to the invention, the plural electric wires may be covered with a jacket, with the spacer being arranged between the jacket and the core-exposing portions.

A connection cable according to the invention includes a cable comprising plural electric wires each comprising a covering portion covering a core and a core-exposing portion exposing the core at an end of the covering portion; and a spacer that is interposed in a space surrounded by the covering portions of the plural electric wires and holds end portions of the covering portions in the state that the end portions are spaced from each other.

According to the invention, it is possible to facilitate work of connecting a cable to a sensor and thus to reduce the manufacturing cost, and also to improve connection accuracy and connection strength.

BRIEF DESCRIPTION OF THE DRAWINGS

Next, the present invention will be explained in more detail in conjunction with appended drawings, wherein:

FIGS. 1A and 1B are explanatory diagrams illustrating an example of a connection structure between a sensor and a multi-core cable in the first embodiment of the present invention, wherein FIG. 1A is an exploded perspective view as viewed in a longitudinal direction and FIG. 1B is an exploded perspective view as viewed in a lateral direction;

FIGS. 3A and 3B are diagrams illustrating the connection structure between the sensor and the multi-core cable of FIGS. 1A and 1B, wherein FIG. 3A is a perspective view as viewed in the longitudinal direction and FIG. 3B is an explanatory diagram illustrating a positional relation between the sensor, a spacer and electric wires;

FIGS. 4A and 4B are explanatory diagrams illustrating an example of the connection structure between the sensor and the multi-core cable in the second embodiment, wherein FIG. 4A is an exploded perspective view as viewed in the longitudinal direction and FIG. 4B is an exploded perspective view as viewed in the lateral direction;

FIGS. 5A and 5B are explanatory diagrams illustrating the spacer and the sensor of FIGS. 4A and 4B, wherein FIG. 5A is a bottom view showing the spacer and FIG. 5B is a top view showing the sensor;

FIGS. 6A and 6B are diagrams illustrating the connection structure between the sensor and the multi-core cable of FIGS. 4A and 4B, wherein FIG. 6A is a perspective view as viewed in the longitudinal direction and FIG. 6B is an explanatory cross-sectional view showing a main part of the assembled sensor and spacer;

FIGS. 7A and 7B are explanatory diagrams illustrating an example of the connection structure between the sensor and the multi-core cable in the third embodiment, wherein FIG. 7A is an exploded perspective view as viewed in the longitudinal direction and FIG. 7B is an exploded perspective view as viewed in the lateral direction;

FIGS. 8A and 8B are explanatory diagrams illustrating the spacer and the sensor of FIGS. 7A and 7B, wherein FIG. 8A is a bottom view showing the spacer and FIG. 8B is a top view showing the sensor;

FIGS. 9A and 9B are diagrams illustrating the connection structure between the sensor and the multi-core cable of FIGS. 7A and 7B, wherein FIG. 9A is a perspective view as viewed in the longitudinal direction and FIG. 9B is an explanatory cross-sectional view showing a main part of the assembled sensor and spacer;

FIGS. 10A to 10C are explanatory diagrams illustrating an example of the connection structure between the sensor and the multi-core cable in the fourth embodiment, wherein FIG. 10A is cross sectional view showing a main part of the multi-core cable, FIG. 10B is a perspective view as viewed in the longitudinal direction, and FIG. 10C is an explanatory cross-sectional view showing a main part of the assembled sensor and spacer; and FIGS. 11A to 11D are longitudinal sectional views showing the spacers used in the invention and including the longitudinal axis thereof, wherein FIG. 11A is a cross sectional view showing the spacer in the first embodiment taken along line A-A of FIG. 1B, FIG. 11B is a cross sectional view showing the spacer in the second embodiment taken along line B-B of FIG. 4B, FIG. 11C is a cross sectional view showing a bullet-shaped spacer in a modification of the first embodiment, and FIG. 11D is a cross sectional view showing a spindle-shaped spacer in another modification.

DETAILED DESCRIPTION OF THE PREFERRED EMBODIMENTS

Figure 2:
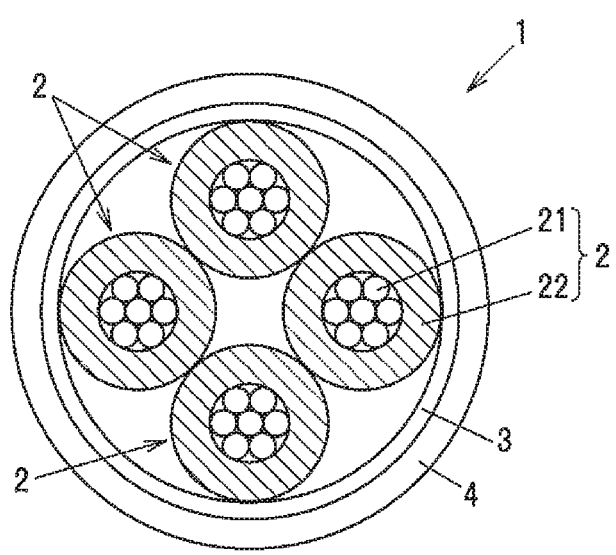
FIG. 2 is a cross sectional view showing a main part of the multi-core cable of FIGS. 1A and 1B.
Figure 5A:
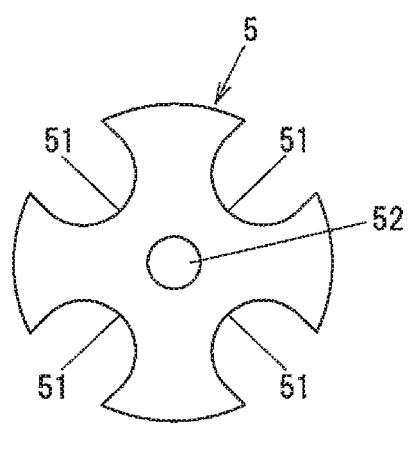
Figure 5B:
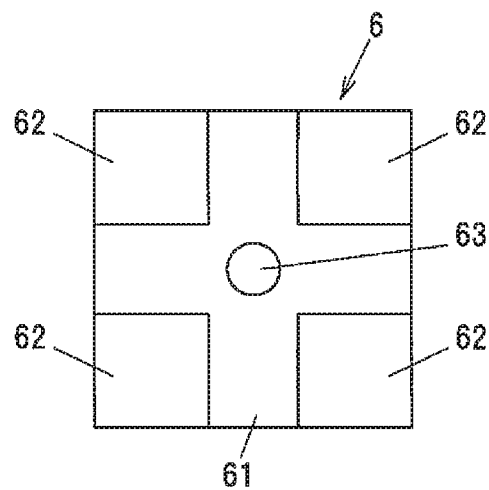
Figure 8A:
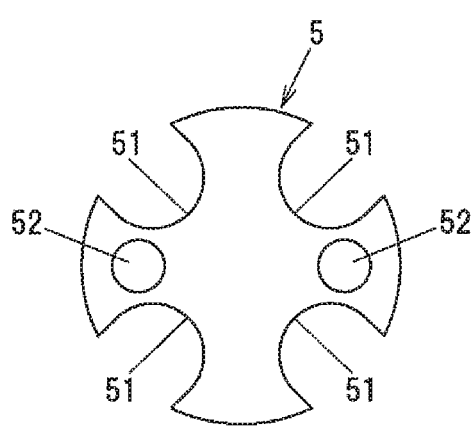
Figure 8B:
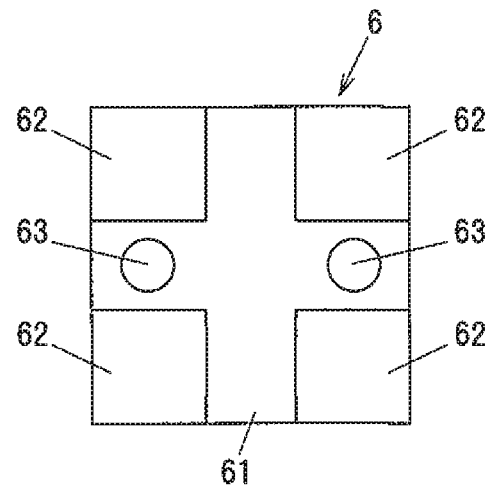

Embodiments of a connection structure between sensor and cable of the invention will be described below in reference to the appended drawings. The scale ratio, etc., of each constituent element is exaggerated from the actual ratio and schematically shown in the appended drawings to facilitate the explanation of the connection structure, and it is not limited to that shown in the illustrated example.

First Embodiment

Connection Structure between Sensor and Cable

A connection structure between a sensor 6 and a cable 1 includes the cable 1 formed by assembling plural electric wires 2 each having a covering portion 22 covering a core 21 and a core-exposing portion 23 exposing the core 21 at an end of the covering portion 22, a spacer 5 which is interposed in a space surrounded by the covering portions 21 of respective electric wires 2 and holds end portions of the covering portions 22 in the state that the end portions are spaced from each other, and the sensor 6 which detects a physical quantity. The core-exposing portion 23 of each electric wire 2 of the cable 1 is electrically connected to the sensor 6 via a fixing member in the state that each electric wire 2 is held by the spacer 5. In FIGS. 1A and 1B, the connection structure between sensor and cable includes the multi-core cable 1 in which the plural electric wires 2 (four in the first embodiment) are bundled into one cable, the spacer 5 holding the plural electric wires 2 which are spaced in a circumferential direction, and the sensor 6 electrically connected to the multi-core cable 1.

Holding the plural electric wires 2 by the spacer 5 here means the state in which each electric wire 2 is fixed to the outer circumferential surface of the spacer 5 by fitting, press-fitting, adhering or welding, etc., to the extent that each electric wire 2 does not move in an axial direction, a radial direction or a circumferential direction.

Multi-core cable 1

As shown in FIGS. 1A, 1B and 2, the multi-core cable 1 is a fine, or super fine, multi-core cable and is used for, e.g., a medical endoscope or a sensor-equipped catheter, etc. The multi-core cable 1 in the illustrated example has a binding tape 3 covering the plural electric wires 2, and a jacket 4 covering the binding tape 3.

The plural electric wires 2 are insulated wires each having the core 21, the covering portion 22 covering and insulating the core 21, and the core-exposing portion 23 at which an end of the core 21 is exposed from a stripped end portion of the covering portion 22. As an example, two of the four electric wires 2 are used as signal lines, one as a power line, and one as a control line.

A very fine strand with a size of not more than AWG (American Wire Gauge) 40 is used as the core 21. The core 21 is a twisted wire composed of plural twisted strands, or a single solid wire, formed of a conductive material such as silver-plated copper alloy. The core 21 shown in the illustrated example is formed from a twisted wire formed by twisting plural strands (seven in the first embodiment). As the covering portion 22, an insulating material such as a fluorine resin (e.g. PFA) material is used without specific limitation.

As the material of the binding tape 3, a resin material such as a polyethylene terephthalate (PET) resin may be used without specific limitation. As the material of the jacket 4, a resin material such as a fluorine resin (e.g. PFA) may be used without specific limitation.

Spacer 5

As shown in FIGS. 1A, 1B, 3A and 3B, the spacer 5 is interposed in a space surrounded by the covering portions 22 of the respective electric wires 2. The plural electric wires 2 may be covered with the jacket 4, and the spacer 5 may be arranged between the jacket 4 and the core-exposing portions 23. The spacer 5 is a molded article which is formed by injection molding of a thermoplastic resin having insulating properties or heat resistance, etc. The thermoplastic resin includes a liquid-crystal polymer (LCP) resin and a polyamide resin, etc.

The spacer 5 is formed in a shape having an outer circumferential surface on which plural holding recesses 51 are provided so as to be spaced in a circumferential direction. In the first embodiment, the spacer 5 has a cylindrical shape, and U-shaped recesses 51 in number corresponding to the electric wires 2 (four in the first embodiment) are formed on the outer circumferential surface of the spacer 5 so as to extend from one end to the other end of the spacer 5 along the axial direction and so as to be arranged side by side on the same circumference at equal intervals. In more detail, the spacer 5 has a rectangular cross section when taken along the longitudinal axis direction and has a substantially cross-shaped cross section when taken along a direction orthogonal to the longitudinal axis direction. The size of the spacer 5 is not specifically limited but is as very small as about 0.5 mm in diameter and about 0.8 mm in length. The size of the recess 51 is set to be slightly smaller than the diameter of the covering portion 22 of the electric wire 2. The depth of the recess 51 at the center in the radial direction is constant from one end to the other end in the first embodiment, but does not necessarily need to be constant, and the recess 51 may be configured such that, e.g., the depth increases toward the cable.

The recess 51 of the spacer 5 keeps the core-exposing portion 23 of each electric wire 2 in the optimal position with respect to the sensor 6. One end of the covering portion 22 of each electric wire 2 is arranged in the recess 51 so that the electric wires 2 are held so as to radiate from the center toward the outside. This allows a large distance to be maintained between the core-exposing portions 23 of the electric wires 2.

Sensor 6

The sensor 6 to be connected to the multi-core cable 1 can be various types of microsensors which detect, e.g., a physical quantity such as voltage, current, magnetism or light and convert it into an electrical signal. Examples of the sensor 6 include an image sensor, such as CCD sensor or CMOS sensor, of a medical endoscope or a sensor-equipped catheter, etc. Alternatively, the sensor 6 may be an infrared sensor or an ultrasonic transducer or a fluorescence sensor. The sensor 6 may be a so-called semiconductor sensor. The sensor 6 may be provided with an image sensor element other than CCD and CMOS.

The sensor 6 in the illustrated example is, but not specifically limited to, a microsensor which is in a square shape when viewed from above and has a side length of about not more than 1.0 mm and a thickness of about not more than 0.5 mm Connecting terminal portions 62 having a square shape when viewed from above are respectively arranged at plural corners (four in the first embodiment) of a substrate 61 of the sensor 6. This allows the plural connecting terminal portions 62 (four in the first embodiment) to be spaced at the maximum distance.

As shown in FIGS. 1A and 3B, two of the four connecting terminal portions 62 of the sensor 6 are used as signal terminal portions, one as a power terminal portion, and one as a control terminal portion. The signal lines of the multi-core cable 1 are respectively electrically connected to the signal terminal portions. The power line of the multi-core cable 1 is electrically connected to the power terminal portion. The control line of the multi-core cable 1 is electrically connected to the control terminal portion.

The core-exposing portion 23 of each electric wire 2 is electrically connected to each connecting terminal portion 62 of the sensor 6 in the state that each electric wire 2 of the multi-core cable 1 is held by the spacer 5. For example, solder, metal paste or conductive adhesive, etc., can be used as a fixing member although it is not shown in the drawings. A connecting member such as laser welding may be also used.

As shown in FIG. 3B, e.g., a center C1 of the core-exposing portion 23 of each electric wire 2 is arranged closer to the middle than a canter C2 of each connecting terminal portion 62 of the sensor 6 when the covering portion 22 of each electric wire 2 is held in the recess 51 of the spacer 5. In the illustrated example, the center C1 of the core-exposing portion 23 of each electric wire 2 is arranged, e.g., about 0.05 mm closer to the middle than the canter C2 of each connecting terminal portion 62 of the sensor 6.

Since the connecting terminal portions 62 of the sensor 6 are provided at the four corners of the substrate 61 of the sensor 6, the connecting terminal portions 62 are spread in a wide region, allowing the largest area to be used as a connection space. Thus, it is possible to provide an enough space around a connecting portion.

To manufacture the connection structure between the sensor 6 and the multi-core cable 1, firstly, the core-exposing portion 23 is formed by cutting a tip portion of the covering portion 22 of each electric wire 2 using, e.g., $CO_2$ laser, as shown in FIG. 1A, etc. Solder and heat are applied to the core-exposing portions 23 which are thus in the state of being connectable by solder. Solder is also applied to each connecting terminal portion 62 of the sensor 6 in the same manner. Alternatively, a heat-resistant flux may be provided on the substrate 61 to eliminate the process of pre-applying solder to the connecting terminal portions 62. Pb-free Sn—Ag—Cu solder, etc., is sued as the solder. In this regard, use of low melting point solder is more desirable to reduce a thermal impact on the sensor. The spacer 5 is provided to interpose between the covering portions 22 of the electric wires 2, and each covering portion 22 is arranged in contact with a bottom surface of the recess 51 of the spacer 5. Next, the core-exposing portion 23 of each electric wire 2 and each connecting terminal portion 62 of the sensor 6, which are in contact with each other, are heated and are thereby soldered to each other. Each core-exposing portion 23 may alternatively electrically and mechanically connected to each connecting terminal portion 62 of the sensor 6 by a fixing member not requiring heating, such as metal paste of Ag, etc., or conductive adhesive, other than the above-described solder connection, as mentioned above. Next, the four electric wires 2, the spacer 5 and the sensor 6 excluding its lower surface are covered with and fixed by a molding resin 7. This completes the connection structure between the sensor 6 and the multi-core cable 1 shown in FIG. 3A. The molding resin 7 is formed of a thermosetting resin such as epoxy resin.

Effects of the First Embodiment

The connection structure between the sensor 6 and the multi-core cable 1 configured as described above exerts the following effects in addition to the effects described above.

Since it is possible to integrate the end portion of the multi-core cable 1 with the spacer 5 by holding the end portion of the multi-core cable 1 in the recesses 51 of the spacer 5, the end portion of the multi-core cable 1 can be easily positioned relative to the sensor 6 and is thus connected to the sensor 6 very easily.

Since adjacent electric wires 2 are prevented from being accidentally pulled and receiving a load during connecting the multi-core cable 1, it is possible to improve connection strength.

Since it is easy to connect the multi-core cable 1 to the sensor 6, it is possible to realize automation by automatic robots and also possible to contribute to improvement in productivity.

Second Embodiment

Referring FIGS. 4A and 4B, the connection structure between the sensor 6 and the multi-core cable 1 in the second embodiment is shown in the drawing.

The configuration in the second embodiment is the same as the configuration in the first embodiment, except the configurations of the spacer 5 and the sensor 6. Therefore, the same members as those in the first embodiment are denoted by the same reference numerals and the detailed explanation thereof will be omitted.

The second embodiment is different from the first embodiment in that a positioning structure is provided to position the spacer 5 with respect to the sensor 6 in the axial direction (the z direction). In more detail, the spacer 5 is formed in a shape having an end face on which a contact portion 52 to be in contact with the sensor 6 is provided. On the other hand, the sensor 6 has a fitting portion 63 as a positioning portion for positioning with respect to the contact portion 52.

In FIGS. 4A, 4B, 5A and 5B, the positioning structure is composed of the raised contact portion 52 formed on an end face of the spacer 5 on the sensor 6 side so as to face the sensor 6, and the recessed fitting portion 63 formed on the sensor 6. The raised contact portion 52 and the recessed fitting portion 63 are arranged on the same axis.

As shown in FIGS. 6A and 6B, the position of the spacer 5 in the axial direction (the z direction) as well as the wiring position between the core-exposing portion 23 of each electric wire 2 and the connecting terminal portion 62 of the sensor 6 can be determined by fitting the raised contact portion 52 into the recessed fitting portion 63.

The positioning structure is not limited to that in the illustrated example and may be composed of a recessed contact portion 52 formed on an end face of the spacer 5 and a raised fitting portion 63 formed on the sensor 6, and may be configured to have a raised portion on either the spacer 5 or the sensor 6.

Effects of the Second Embodiment

The connection structure between the sensor 6 and the multi-core cable 1 in the second embodiment configured as described above exerts the same effects as those in the first embodiment and also exerts the following effects.

The sensor 6 and the end portion of the multi-core cable 1 are connected in an ideal position and the sensor 6 is also mechanically connected and fixed to the spacer 5, hence, it is possible to further improve positioning accuracy, connection accuracy and connection strength.

Third Embodiment

Referring FIGS. 7A and 7B, the connection structure between the sensor 6 and the multi-core cable 1 in the third embodiment is shown in the drawing. In FIGS. 7A and 7B, the members substantially the same as those in the first embodiment are denoted by the same names and the same reference numerals. Therefore, the detailed explanation of such members will be omitted.

While the positioning structure in the second embodiment is provided to position the spacer 5 with respect to the sensor 6 in the axial direction (the z direction), the third embodiment is different from the second embodiment in that the positioning structure is provided to position the spacer 5 with respect to the sensor 6 in a front-to-back and side-to-side direction (the XY direction) and a rotational direction (a θ direction) in addition to the axial direction (the z direction).

In FIGS. 7A, 7B, 8A, 8B, 9A, and 9B, the positioning structure is composed of a pair of raised contact portions 52, 52 formed on the end face of the spacer 5 and a pair of recessed fitting portions 63, 63 formed on the sensor 6. The pair of raised contact portions 52 are respectively arranged on the same axes as the pair of recessed fitting portions 63.

The position of the spacer 5 in the axial direction (the z direction), in the front-to-back and side-to-side direction (the XY direction) and in the rotational direction (the θ direction) as well as the wiring position between the core-exposing portion 23 of each electric wire 2 and the connecting terminal portion 62 of the sensor 6 can be determined by fitting the pair of raised contact portions 52 into the pair of recessed fitting portions 63.

Effects of the Third Embodiment

The connection structure between the sensor 6 and the multi-core cable 1 in the third embodiment configured as described above exerts the following effects in addition to the same effects as those in the first embodiment.

Since it is possible to position the spacer 5 in the axial direction, in the front-to-back and side-to-side direction and the rotational direction, it is possible to further improve accuracy of fixing the wiring position of the end portion of the multi-core cable 1 with respect to each connecting terminal portion 62 of the sensor 6 and thus to also further improve workability.

Fourth Embodiment

Referring FIGS. 10A to 10C, an explanatory diagram for explaining the connection structure between the sensor 6 and the multi-core cable 1 in the fourth embodiment is shown in the drawing.

The fourth embodiment is different from the first embodiment in that a shield layer for reducing noise is provided. The configuration is substantially the same as that in the first embodiment, except a part of the configuration of the multi-core cable 1, a part of the configuration of the spacer 5 and a part of the configuration of the sensor 6. Therefore, the same members as those in the first embodiment are denoted by the same reference numerals and the detailed explanation thereof will be omitted.

As shown in FIG. 10A, the multi-core cable 1 is composed of a pair of coaxial wires 8, 8, a pair of electric wires 2, 2, the binding tape 3 covering the wires 2, 8, an outer shield 9 covering the binding tape 3, and the jacket 4 covering the outer shield 9. The pair of coaxial wires 8 are both signal lines. The pair of electric wires 2 are respectively a power line and a control line.

Each coaxial wire 8 is composed of a core 81, a covering portion 82 covering and insulating the core 81, a core-exposing portion 86 not covered with the covering portion 82, an inner shield 83 covering the covering portion 82, and an outer covering portion 84 covering the inner shield 83. An end portion of the inner shield 83 is a shield-exposed portion 85 not covered with the outer covering portion 84. Each coaxial wire 8 serves as a shield to prevent electrical interference and is thus used as a shield wire.

A very fine strand with a size of, e.g., not more than AWG 46 is used as the core 81. The core 81 is a twisted wire composed of plural twisted strands, or a solid wire, formed of a conductive material such as silver-plated copper alloy. As the covering portion 82, an insulating material such as a fluorine resin (e.g. PFA) material may be used. The inner shield 83 is configured that fine metal wires such as silver-plated copper alloy wires are spirally wound around the covering portion or are braided and wrapped around the covering portion. As the outer covering portion 84, an insulating material such as a fluorine resin (e.g. PFA) may be used.

The material of the binding tape 3 is a resin material such as a polyethylene terephthalate (PET) resin, etc. The outer shield 9 is configured that fine metal wires such as tin-plated soft copper wires are spirally wound around the binding tape 3 or are braided and wrapped around the binding tape 3.

It is preferable that the surface of a spacer 55 be electrically conductive. When the electric wire 2 is a shield wire provided with a shield layer, the shield layer can be electrically connected to the conductive surface of the spacer 55.

As shown in FIGS. 10B and 10C, the connection structure between the sensor 6 and the multi-core cable 1 includes the conductive spacer 55. The spacer 55 may include a resin spacer of which surface is covered with a conductive material made of metal plating of gold or copper, etc., or a metal spacer formed of a conductive material. Even when using a metal spacer, a metal plating may be applied to the formed spacer to increase conductivity of the surface of the spacer.

Plural U-shaped recesses 56 (four in the fourth embodiment) are formed on the outer circumferential surface of the conductive spacer 55 and are arranged side by side on the same circumference at equal intervals. In the recesses 56, the covering portion 22 of each electric wire 2 is held and the shield-exposed portion 85 of each coaxial wire 8 is held in the electrically connected state. In addition, by electrically connecting a portion of the outer shield 9 to the conductive spacer 55, each electric wire 2 and each coaxial wire 8 can be shielded together from external surge, etc.

Meanwhile, a raised ground terminal portion 64 connected to a ground line (not shown) is provided on the substrate 61 of the sensor 6. One end face of the conductive spacer 55 is electrically connected to the ground terminal portion 64 of the sensor 6. Each connecting terminal portion 62 of the sensor 6 is electrically connected to the core-exposing portion 23 of each electric wire 2 or the core-exposing portion 86 of each coaxial wire 8 by solder, metal paste or conductive adhesive, etc., which is not shown in the drawings.

When the conductive material of the conductive spacer 55 is connected to the ground terminal portion 64 of the sensor 6, the conductive spacer 55 is at a ground potential or a common potential. The ground terminal portion 64 can also serve to position the conductive spacer 55 with respect to the sensor 6 in the axial direction (the z direction).

Effects of the Fourth Embodiment

The connection structure between the sensor 6 and the multi-core cable 1 in the fourth embodiment configured as described above exerts the following effects in addition to the same effects as those in the first embodiment.

Since the conductive spacer 55 can be kept at a ground potential or a common potential by connecting the conductive material on the conductive spacer 55 to the ground terminal portion 64 of the sensor 6, noise is reduced by connecting the shield-exposed portion 85 of each coaxial wire 8 to the conductive spacer 55 and improvement in electrical characteristics can be expected.

Modifications of Spacer

Figure 11A:
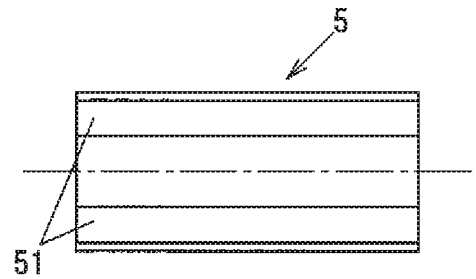
Figure 11B:
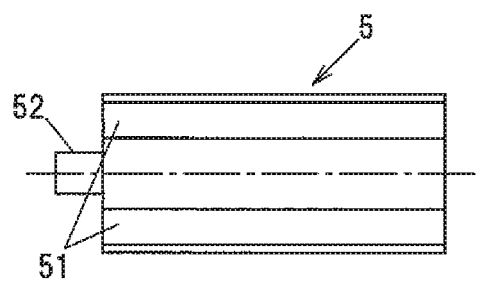
Figure 11C:
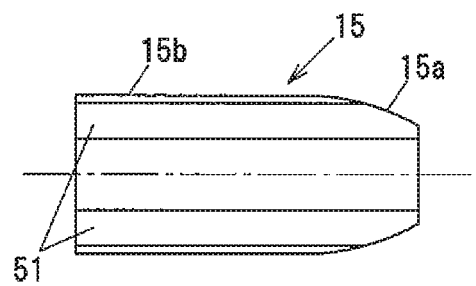
Figure 11D:
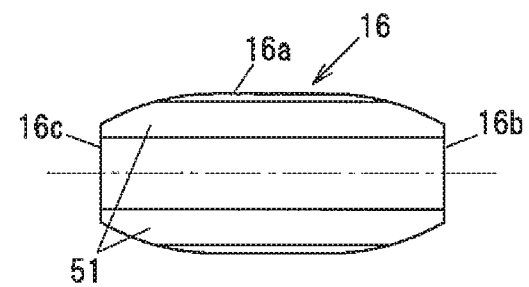

FIGS. 11A to 11D are longitudinal sectional views showing the spacers used in the invention and including the longitudinal axis thereof, wherein FIG. 11A is a cross sectional view showing the spacer in the first embodiment taken along line A-A of FIG. 1B, FIG. 11B is a cross sectional view showing the spacer in the second embodiment taken along line B-B of FIG. 4B, FIG. 11C is a cross sectional view showing a bullet-shaped spacer in a modification of the first embodiment, and FIG. 11D is a cross sectional view showing a spindle-shaped spacer in another modification.

As shown in FIG. 11A, the spacer 5 in the first embodiment is in a cylindrical shape, has a rectangular cross section when taken along the longitudinal direction and has a substantially cross-shaped cross section when taken along a direction orthogonal to the longitudinal direction.

As shown in FIG. 11B, the spacer 5 in the second embodiment has a configuration in which the raised contact portion 52 is additionally formed on the spacer 5 in the first embodiment on the sensor 6 side. The spacers 5, 55 in the third and fourth embodiments also have a configuration in which the raised contact portion(s) 52 is/are formed in the same manner.

As shown in FIGS. 11C and 11D, the outer diameter of the spacer does not need to be constant from one end to the other. As shown in FIG. 11C, a spacer 15 may have a bullet shape which is tapered toward an end on the multi-core cable 1 side. The cross section of such a spacer 15 taken along the longitudinal direction has a trapezoidal shape with an arc-shaped side 15a on the multi-core cable 1 side and a rectangular shape with a side 15b on the sensor 6 side.

Meanwhile, as shown in FIG. 11D, a spacer 16 may have a spindle shape which has a largest outer diameter at a middle portion 16a and is tapered toward an end portion 16b on the multi-core cable 1 side as well as toward an end portion 16c on the sensor 6 side. The cross section of such a spacer 16 taken along the longitudinal direction has a trapezoidal shape with two arc-shaped sides on the multi-core cable 1 side and a trapezoidal shape with two arc-shaped sides on the sensor 6 side, and is thereby symmetric with respect to a line in the width direction orthogonal to the longitudinal direction.

In these cases, the recesses 51 may be partially provided between one end and the other. Furthermore, in case of the spacers 15 and 16 configured to be tapered toward the end on the multi-core cable 1 side, the spacer 5 may be configured such that the end portion on the multi-core cable 1 side partially extends inside the multi-core cable 1.

The application of the connection structure between the sensor 6 and the multi-core cable 1 is not limited to the medical field such as medical endoscope or sensor-equipped catheter. For example, it is applicable to endoscope sensors for industrial equipment, particularly to equipment for testing a device provided with a minute structure. The connection structure between the sensor 6 and the multi-core cable 1 has a configuration applicable in various field, e.g., the electronic device field such as motor, the optical device field such as camera, the robot field, the automobile field, and the information processing field such as security, etc., particularly when a microsensor is connected to a super fine cable.

Although the representative embodiments, modifications, and illustrated examples according to the invention have been exemplified, it is obvious from the above description that the invention according to claims is not to be limited to the above-mentioned embodiments, modifications, and illustrated examples and can be implemented in various aspects without departing from the gist of the invention. Therefore, it should be noted that all combinations of the features described in the embodiments, modifications, and illustrated examples are not necessary to solve the problem of the invention.

What is claimed is:

1. A connection structure between sensor and cable, comprising:
    a cable comprising a plurality of electric wires each comprising a covering portion covering a core and a core-exposing portion exposing the core at an end of the covering portion;
    a spacer that is interposed in a space surrounded by the covering portions of the electric wires and holds end portions of the covering portions in the state that the end portions are spaced from each other; and
    a sensor that detects a physical quantity,
    wherein the spacer includes a plurality of holding recesses for holding a surface of the covering portion of each of the electric wires therein by directly press-fitting,
    wherein the core-exposing portion of each of the electric wires of the cable is electrically connected to the sensor via a fixing member in the state that the surface of the covering portion of each of the electric wires is held by directly press-fitting into each of the holding recesses of the spacer,
    wherein the end portions of the covering portions are integrated with the spacer by directly press-fitting, and
    wherein a diameter of the holding recesses is smaller than a diameter of the covering portion of the electric wire.

2. The connection structure between sensor and cable according to claim 1, wherein each of the holding recesses has a U-shaped cross section, and wherein the spacer has an outer circumferential surface on which the plurality of holding recesses are spaced from each other in a circumferential direction.

3. The connection structure between sensor and cable according to claim 1, wherein the spacer has an end face on which a contact portion configured to be in contact with the sensor is provided.

4. The connection structure between sensor and cable according to claim 3, wherein the sensor comprises a positioning portion for positioning with respect to the contact portion.

5. The connection structure between sensor and cable according to claim 1, wherein a surface of the spacer is electrically conductive.

6. The connection structure between sensor and cable according to claim 1, wherein the fixing member comprises solder, metal paste, conductive adhesive or laser welding.

7. The connection structure between sensor and cable according to claim 1, wherein the sensor comprises a CCD sensor or a CMOS sensor.

8. The connection structure between sensor and cable according to claim 5, wherein, when the electric wire comprises a shield wire comprising a shield layer, the shield layer is electrically connected to the conductive surface of the spacer.

9. The connection structure between sensor and cable according to claim 1, wherein the plurality of electric wires are covered with a jacket, and the spacer is arranged between the jacket and the core-exposing portions.

10. A connection cable, comprising:
    a cable comprising a plurality of electric wires each comprising a covering portion covering a core and a core-exposing portion exposing the core at an end of the covering portion; and
    a spacer that is interposed in a space surrounded by the covering portions of the electric wires and includes a plurality of holding recesses in which a surface of the covering portion of each of the electric wires is held by directly press-fitting while end portions of the covering portions are held in the state that the end portions are spaced from each other,
    wherein the plurality of holding recesses are arranged side by side on a same circumference of the spacer at equal intervals,
    wherein the end portions of the covering portions are integrated with the spacer by directly press-fitting, and
    wherein a diameter of the holding recesses is smaller than a diameter of the covering portion of the electric wire.

11. The connection structure between sensor and cable according to claim 1, wherein the cable further comprises a coaxial wire comprising a core wire, an inner covering portion, a shield, and an outer covering portion.

12. A method for manufacturing a connection structure between a sensor that detects a physical quantity and a cable comprising a plurality of electric wires each comprising a covering portion covering a core and a core-exposing portion exposing the core at an end of the covering portion, the method comprising:
    preparing a spacer including a plurality of holding recesses for holding a surface of the covering portion of each of the electric wires therein by directly press-fitting;
    interposing the spacer in a space surrounded by the covering portions of the electric wires and directly press-fitting the covering portion of each of the electric wires into each of the holding recesses; and
    electrically connecting the core-exposing portion of each of the electric wires to the sensor via a fixing member,
    wherein the end portions of the covering portions are integrated with the spacer by directly press-fitting, and
    wherein a diameter of the holding recesses is smaller than a diameter of the covering portion of the electric wire.

13. The connection structure between sensor and cable according to claim 1, wherein the surface of the covering portion of each of the electric wires is held in direct contact with a bottom surface of the holding recesses of the spacer.

14. The connection cable according to claim 10, wherein the surface of the covering portion of each of the electric wires is held in direct contact with a bottom surface of the holding recesses of the spacer.

15. The connection cable according to claim 10, wherein the cable further comprises a coaxial wire comprising a core wire, an inner covering portion, a shield, and an outer covering portion.

16. The method for manufacturing a connection structure according to claim 12, wherein the surface of the covering portion of each of the electric wires is held in direct contact with a bottom surface of the holding recesses of the spacer.

17. The method for manufacturing a connection structure according to claim 12, wherein the cable further comprises a coaxial wire comprising a core wire, an inner covering portion, a shield, and an outer covering portion.

18. The connection structure between sensor and cable according to claim 1, wherein the plurality of holding recesses are arranged side by side on a same circumference of the spacer at equal intervals.

19. The connection structure between sensor and cable according to claim 1, wherein each of the plurality of holding recesses keeps the core-exposing portion of each of the electric wires in an optimal position with respect to the sensor.

20. The connection structure between sensor and cable according to claim 1, wherein the end of the covering portion of each of the electric wires is arranged in each of the plurality of holding recesses in such a manner that the electric wires are held to radiate outwardly from a center.

21. The connection structure between sensor and cable according to claim 1, wherein the end portions of the covering portions of the electric wires are integrated with the spacer only by the directly press-fitting and devoid of any connecting, attaching or joining material at a time of positioning, so that movement in an axial direction of the electric wires is suppressed.

22. The connection cable according to claim 10, wherein the end portions of the covering portions of the electric wires are integrated with the spacer only by the directly press-fitting and devoid of any connecting, attaching, or joining material at a time of positioning, so that movement in an axial direction of the electric wires is suppressed.

23. The method for manufacturing a connection structure according to claim 12, wherein the end portions of the covering portions of the electric wires are integrated with the spacer only by the directly press-fitting and devoid of any connecting, attaching, or joining material at a time of positioning, so that movement in an axial direction of the electric wires is suppressed.

* * * * *